US005669393A

United States Patent [19]
Faisandier

[11] Patent Number: 5,669,393
[45] Date of Patent: Sep. 23, 1997

[54] PROGRAMMABLE INTERFACE FOR A PHYSIOLOGICAL SIGNAL RECORDING DEVICE

[75] Inventor: Yves Faisandier, Paris, France

[73] Assignee: ELA Medical S.A., Montrouge, France

[21] Appl. No.: 562,290

[22] Filed: Nov. 22, 1995

[30] Foreign Application Priority Data

Nov. 22, 1994 [FR] France ................... 94 13952

[51] Int. Cl.⁶ ........................................ A61B 5/04
[52] U.S. Cl. ............................ 128/710; 128/709
[58] Field of Search ..................... 128/696, 709, 128/710; 364/413.06; 395/889, 890

[56] References Cited

U.S. PATENT DOCUMENTS

| 4,695,955 | 9/1987 | Faisandier ............... 364/413 |
| 5,012,411 | 4/1991 | Policastro et al. ......... 364/413.06 |

FOREIGN PATENT DOCUMENTS

| 356603 | 3/1990 | European Pat. Off. ........ 128/696 |
| 488410 | 6/1992 | European Pat. Off. ........ 128/696 |
| 0 581 073 | 7/1993 | European Pat. Off. . |
| 2 557 318 | 12/1983 | France . |

OTHER PUBLICATIONS

Driscoll et al., "Data Acquisition and Process Control with the M68HC11 Microcontroller" MacMillan Publishing Co 1994.

"MC68HC11A8—HCMOS Single Chip Microcontroller" Motorola Inc 1991.

Primary Examiner—William E. Kamm
Assistant Examiner—George R. Evanisko
Attorney, Agent, or Firm—Orrick, Herrington & Sutcliffe, LLP

[57] ABSTRACT

A programmable interface for typical Holter machine for recording a physiological signal, notably of cardiac activity. This apparatus (10) comprises the normal plugs (14) for connection to external electrodes and a processing circuit (20) for acquiring and recording the physiological signal, and a programmable interface comprising: at least one voltage supply plug (and preferably two supply plugs V+, V-), at least one ground plug, at least one digital plug (preferably two or more digital plugs D1, D2), cooperating with the processing circuit (20), at least one analog/digital mixed plug (A/D3), on the one hand connected to an analog signal input of the machine, and on the other hand cooperating with the aforementioned processor circuit, and a logic circuit (28) for programming the interface to transfer signals through the plugs of the interface.

21 Claims, 1 Drawing Sheet

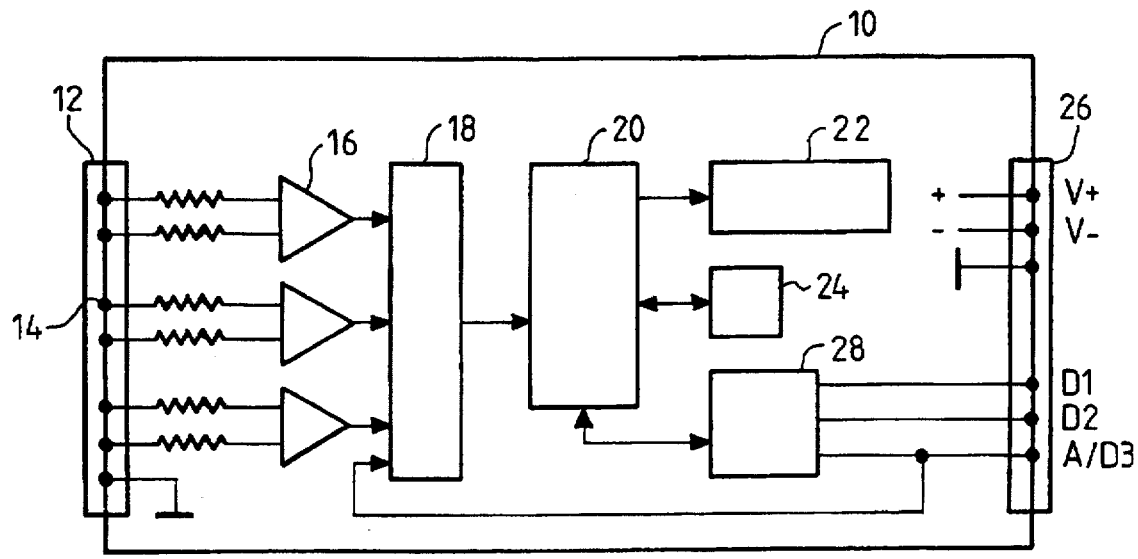
FIG_1
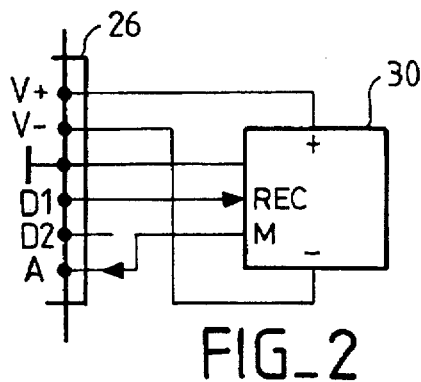
FIG_2
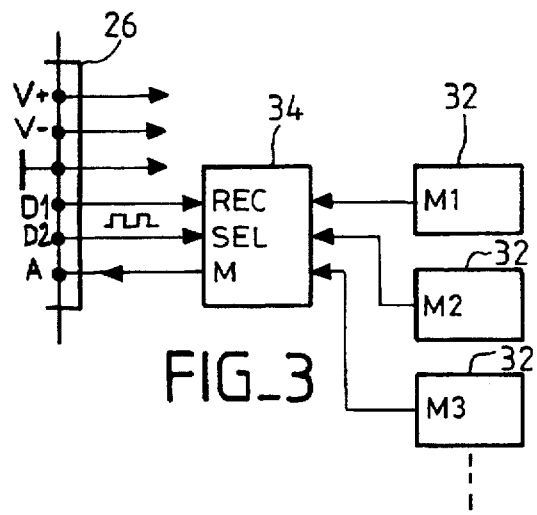
FIG_3
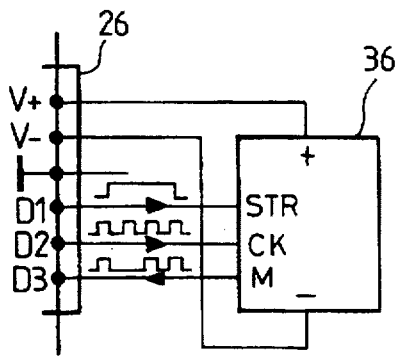
FIG_4
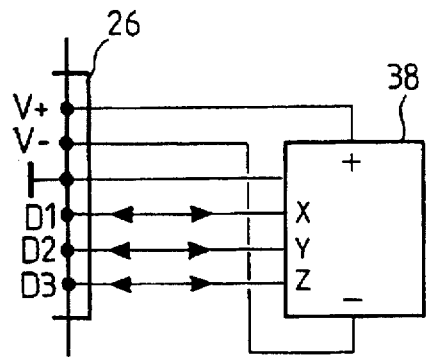
FIG_5

PROGRAMMABLE INTERFACE FOR A PHYSIOLOGICAL SIGNAL RECORDING DEVICE

FIELD OF THE INVENTION

The invention concerns, in a general manner, remote monitoring of physiological parameters, notably of cardiac activity, undertaken by means of a so-called "Holter" recorder. A Holter recorder is a machine that records, virtually continuously and over a long time period, signals sensed by means of electrodes applied on a patient.

BACKGROUND OF THE INVENTION

As recognized by the inventor, in many cases, it would be interesting, with a Holter recording device, to expand the measurement to other sensors (i.e., sensors in addition or in the alternative to the sensors that are typically used in such a Holter recorder) or, more generally, to provide communications with other ambulatory systems carried by, or implanted in, the patient.

There are various known ways of interfacing such a multiple sensor system, using a mini-network, an RS-232 protocol, etc. The diversity in interface possibilities renders the choice difficult if one wants to preserve a very large variety of extension possibilities.

Furthermore, these known interfacing processes and structures, which all rest on the exchange of digital data through the interface, are complex enough to implement, such that when one wishes to complete the system extension to include one or more analog sensors, there are added complexities, including the transmission of analog signal through the interface, and the additional risk of an increased energy consumption, which is incompatible with the desired autonomy of the source of energy (battery) of the machine.

OBJECTS AND SUMMARY OF THE INVENTION

One of objects of the present invention is to provide an interface for a typical Holter recorder machine which is destined to receive signals coming from supplementary sensors other than the sensors conventionally used in Holter recordings, namely electrodes that sense cardiac activity. These additional signals are able to come from such supplementary sensors of a varied nature (i.e, they may be digital and/or analog) and moderate in number (one, several or more additional supplementary sensors), but by means of one and the same interface, and without it being necessary to modify further the circuits of the recording machine or their internal cabling to accommodate the different supplemental sensors.

Another object of the invention, in addition to the collection of signals by supplementary sensors, is to obtain a possibility of controlling an external system (e.g., an implanted or ambulatory medical machine, communication device, etc.), with the same interface that is used in other instances to collect signals from supplemental sensors.

To this end, the present invention broadly concerns providing a Holter recording apparatus with a mixed interface (analog and digital) that is rendered programmable by an appropriate logic circuit, allowing the interface to be configured in a particular form for performing a needed function simply by an application of appropriate logic control signals, without requiring modification of the hardware configuration of the basic Holter recording machine.

One aspect of the invention concerns a programmable interface for a typical Holter machine having a number of connection plugs to one or more external electrodes, comprising:

at least a voltage supply plug;

at least one ground plug;

at least one digital plug, more preferably two digital plugs, cooperating with the processing means (e.g., solid state logic machine (FGPA), computer, microcontroller, or microprocessor system) of the Holter machine;

at least one mixed analog/digital plug (also referred to herein as a "MAD plug" or a "mixed plug") which is on the one hand connected to an analog signal input of the Holter machine, and on the other hand operatively connected to the aforementioned processing means; and a logic circuit connected to the interface and operable to program the transfer mode of signals by at least certain of the interface plugs.

Preferably, the logic circuit comprises a programmable logic circuit system which is notably operable to program the mixed plug to be one of an analog plug to receive an analog sensor output signal, a digital plug to receive a digital sensor output signal, and an output plug for outputting a control signal (typically a digital output, but not excluding the possibility of analog output signals) to an external circuit. The logic circuit is furthermore operable to program at least one of said digital plugs to be a signal input plug of a sensor, an output for a control signal from an external circuit, a sensor recognition plug for emitting an interrogation signal to the sensor in a manner that the former, if it is present, provokes a response at another interface plug at a predetermined value, and/or a plug emitting a selection code to a multiplexing circuit to select one of a plurality of sensors, a plug emitting a sampling demand code to a digital sensor, a plug emitting a synchronization clock signal to a digital sensor. When more than one digital plug $D_i$ ( $>1$ ) is used, the different digital plugs may be programmed with different signal transfer functions (e.g., input, output, bidirectional) depending on the application of the modified Holter recording device having the programmable interface of the present invention. It should be understood that the ground plug and V+ and V− voltage supply plugs may be dedicated or programmable, as a matter of design choice.

Advantageously, the present invention provides an improved Holter device, including a microprocessor, logic circuit, analog processing circuit, digital processing circuits, analog-to-digital conversion, and memory, which is preferably formed as a single integrated hybrid circuit chip (or alternately as a limited number of such chips), which can be manufactured in large quantities and differently programmed for use in a wide variety of sensing and/or control applications. This results in a programmable device that is lower in manufacturing cost and useful in a large number of applications, in addition to mere Holter recording.

BRIEF DESCRIPTION OF THE DRAWINGS

Others characteristics and advantages of the invention will appear to the person of ordinary skill in the art in view of the detailed description below of an example of a preferred embodiment of the invention, made with reference to drawings annexed, in which:

FIG. 1 is a block diagram showing the internal structure of a Holter recording machine incorporating the invention;

FIG. 2 is a schematic diagram of a unique analog sensor, connected to the programmable interface of FIG. 1;

FIG. 3 is a schematic diagram of a plurality of multiplexed analog sensors connected to the programmable interface of FIG. 1;

FIG. 4 is a schematic diagram of a digital sensor connected to the programmable interface of FIG. 1; and FIG. 5 is a schematic diagram of an active external system controlled by a Holter recording machine via the interface of FIG. 1 to which it is connected in accordance with an embodiment of the present invention.

DETAILED DESCRIPTION OF THE DRAWINGS

Referring to FIG. 1, a typical Holter recording apparatus 10 is generally shown. This machine comprises a certain number of circuits, in themselves well known, allowing the acquisition and recording of a physiological signal and the control of the machine. The particular structure of a Holter recording machine does not form a part of the present invention and therefore will not be described in detail. Virtually any Holter recording machine (or indeed any ambulatory physiological signal recording device) may be modified to implement the present invention as described herein. One suitable Holter machine embodying the invention is the Model Synesis, available from ELA Medical, Montrouge, France, the Assignee of this invention.

The Holter recording machine 10 includes a first connector 12 with a plurality of plugs 14, typically having seven plugs, (six for acquiring the physiological signals and one for a ground return). Each of plugs 14 is connected, on the one hand, to a cable connected to an electrode applied on a patient to allow the physiological signal collection and, on the other hand, to an input of an amplifier 16 whose output is applied to an analog input of an analog-to-digital converter ("ADC") 18 insuring the conversion, the sampling and the multiplexing of the different amplifier output signals. These digitized signals are then processed by a processor circuit 20, that operates a display 22 and a large capacity memory 24. The memory 24, which in actuality may be one or more memory devices, includes a block of memory for data storage and preferably a block of memory for storage of the software for operating the Holter device and the data for the programmable interface.

According to the invention, the machine 10 comprises a second connector 26 which is a programmable interface to supplementary sensors and/or external systems. As used herein, the adjectives supplementary, additional and complementary are used synonymously when applied to the nouns sensor and parameter.

In the illustrated embodiment, the programmable interface connector 26 includes six plugs, namely: (1) a plug having a positive supply voltage (V+), for example, 2.5 volts; (2) a negative supply voltage plug (V−), for example, −2.5 volts; (3) a ground return plug (G); (4) a first digital plug (D1); (5) a second digital plug (D2); and (6) a mixed analog/digital plug (A/D3).

The three plugs D1, D2 and A/D3 are the programmable plugs. In this regard, each is connected to a logic circuit 28 which provides the programming of the plugs by issuing suitable control signals to control the interconnection of each plug for its intended function. A typical logic circuit 28 is preferably a programmable logic circuit system of a known type, for example, a circuit sold under the mark XLINX Model: XC3030, available from XLINK, San Jose Calif. or a comparable programmable solid state machine device. The path's contained in this circuit are programmed to connect the machine 10 for a transfer of a set of data from the processor circuit 20 to the programmable logic system 28.

Signals received on the three programmable plugs D1, D2, A/D3 are applied by the intermediary of the logic circuit 28 to the processor circuit 20, where they will be processed in a desired and appropriated manner; conversely, plugs D1, D2, A/D3 also can function as an output for the dispatch of control signals or for controlling an external system; they receive in this latter case appropriate signals from the processor circuit 20 by the intermediary of the logic circuit 28.

The mixed plug A/D3, in addition to its connection to the circuit 28 (a digital plug function), is connected to an analog input AN of the analog-to-digital converter 18. Thus, an input signal applied at the input of the plug A/D3 will be able to be processed in the same general manner as the physiological signals delivered by amplifiers 16. Concerning this mixed plug A/D3, it will be designated "A" in the following description when it will be programmed to function as an analog plug, and "D3" when it will be programmed to function as a digital plug. In this latter case, one will note that it can be used and programmed to act in the same manner as the two other digital plugs D1 and D2, and thus presents no specific character as compared to them.

Referring to FIGS. 2 to 5, various sensor configurations and external systems susceptible to be connected to the connector 26 of the Holter machine, to cooperate with the programmable interface of the present invention, are shown.

FIG. 2 illustrates the case of a single analog sensor 30 connected to connector 26. This sensor 30 is supplied by one voltage (V+) or optionally by two voltages (V+ and V−), and the ground plug G. The output voltage that Sensor 30 delivers at an output M is sensed directly on plug A for transfer through the interface. Because this is the measured voltage that will be applied at the analog input AN of the analog-to-digital converter 18 of the Holter recording machine, the device is able to process and possibly to memorize (i.e. store in the memory) the complementary sensed parameter delivered by the additional sensor 30.

As is apparent from the circuit illustrated in FIG. 1, ADC 18 may include a multiplexing function wherein a plurality of analog inputs exist, and one input at a time is sampled for conversion. It should be understood that such a circuit may be replaced with a discrete multiplexor and analog-to-digital converter, as is known in the art.

Advantageously, one of the digital plugs, for example, the plug D1, can be used as a recognition signal plug to determine the presence or absence of a complementary sensor connected to the connector 26. To this end, the Holter machine 10, at the moment it is turned on and possibly at regular intervals for control, sends to the plug D1, which is normally biased at the level logic '0', a level '1' signal that is transmitted to the recognition input REC of the sensor 30. This signal will have for an effect to force the output M of sensor 30 to a predetermined value, for example, a voltage equal to the voltage V+. Thus, according to whether or not the voltage appearing at plug A in response to the recognition signed is at the predetermined value, the machine 10 determines whether or not a sensor 30 is connected and adapts its functioning correspondingly.

More generally, this automatic recognition system can be used to determine not only the presence or the absence of a sensor 30 or an external system on the interface connector 26, but also can indicate to the system the configuration of the sensor or system that is connected. In this regard, for example, if the appearing signal is a simple '1' (voltage V+), this means the presence of a unique analog sensor. On the other hand, the appearance of a more complex signal, such as a digital data word in series, means the presence of an external system (analog or digital) that is more complex than the single analog sensor.

In this way, the machine 10 will be able to select automatically the appropriate configuration of the programmable circuit 28 as a function of the type of sensor or external system recognized. The machine also will be able to initialize in the software of the processor circuit 20 using parameters corresponding to the configuration thus recognized (which parameters may differ from one configuration to another).

The circuit illustrated in FIG. 3 presents the case of a plurality of analog sensors 32, moderate in number, delivering analog signals on their respective outputs M1, M2 and M3 (only three such analog sensors 32 are shown). An intermediate circuit 34 assumes a role of multiplexing and initial coding of the processor 20 and/or logic circuit 28 for the plurality of sensor configurations.

Circuit 34 thus includes a recognition input REC, a select input SEL and a multiplexed output M of the selected measured signal. One or more of plugs V+ and V− may be used for powering the sensors 32 and the circuit 34.

The application of a level '1' signal on plug D1, transmitted to the plug REC of the circuit 34, allows the automatic recognition of this configuration. For example, the circuit 34 in response delivers at its output M a digital word in series, identifying the nature of the particular analog system connected to the interface connector 26. From these indications, the machine 10 controls the multiplexing by the dispatch of a digital word in series on the output D2, transmitted to the selection input SEL of the circuit 34.

The voltage at output $M_i$ of the selected sensor $32_i$ is then transmitted by circuit 34 to the output plug M of circuit 34, and then to the analog input plug A of the Holter recording machine, and then to the analog input AN of the analog-to-digital converter 18. The analog output dynamic range sensor 32 is preferably in accordance with the dynamic range of the analog-to-digital converter, e.g., limited by V+ and V−. When appropriate however, a voltage divider using a variable resistance, e.g., a manually or a microprocessor controlled potentiometer, may be used to scale the selected sensed complementary analog signal so that it is within the range of analog-to-digital converter 18 for conversion. The recognition signal response may be used to control automatically the scaling of the analog signal.

This configuration is, for example, particularly advantageous and interesting when one wishes to use the Holter recording device for the collection of electroencephalogram (EEG) signals, which signals typically require ten or twenty electrodes to measure the EEG and therefore require more leads than the conventional Holter device connector 12, which is limited to three differential leads (or six plugs).

The circuit in FIG. 4 illustrates the case of a digital sensor 36 connected on the connector 26. This sensor comprises a sampling control input STR, a measured signal output M, and possibly a synchronization input CK. These three plugs of sensor 36 are respectively connected to plugs D1, D2 and D3 of interface connector 26 of the Holter recording machine 10. The sensor 36 may also receive supply voltages V+ and V− and be coupled to the ground plug G.

The sensor 36 thus delivers measurement data to the input D3 in the form of a digital word transmitted in series. These data streams are serially transmitted to the processor circuit 20 by the intermediary of the logic circuit 28. It is to be understood that the digital word alternately may be transmitted in parallel by the use of additional measured signal plugs $M_i$ for an i bit word and a corresponding number of plugs $D_i$ on the machine 10. A buffer may be used to receive the parallel words until the data can be processed and/or stored in a memory. Logic circuit 28 may be configured to permit using plugs D1, D2 and D3 to receive 3 bit digital values from sensor 36 in parallel, and to use plugs D1 and D2 to output the STR and CK signals to sensor 36 to trigger a digital output from sensor 36. Of course, when greater signal resolution is required as is typical in physiological signals, more than three plugs may be used to transfer words larger than 3 bit words in parallel, e.g., 5 or 8 plugs for 5 bit or 8 bit words.

The extension of the present invention to a plurality of digital sensors is of course possible and within the ability of a person of ordinary skill in the art, using, for example, a similar diagram to that shown with the single sensor. The various sensors may then be connected in parallel to the connector 26, for example, by the intermediary of a data communication bus. In this case, the sampling control signal STR includes a plurality of specific data codes, with one code uniquely identifying each of the plurality of sensors 36.

The sensor 36, when it receives its specific identification code will recognize it and, in response, transfer its data on the output plug D3 via the bus (not shown). The outputs of the other non-selected sensors 36 will remain at a high impedance outside of the transmission periods (one uses to this end a "three state" logic). Thus, each sensor 36 transfers its data only in response to a sample control signal STR identifying that sensor by its unique identification code.

The machine 10 has of course to use a process capable of identifying the different sensors 36 by codes to avoid collisions, by managing in an appropriate manner the exchange of data between the machine 10 and the sensors 36. One can especially use to this end a communication switchboard protocol such that the switchboard known as model I2C available from PHILIPS N.V., (Eindoven, The Netherlands).

The present invention also may be extended to an embodiment in which there are a plurality of analog signal sensors which are coupled to an alternate circuit 34 which, in addition to performing the multiplexing functions described above with reference to FIG. 3, also performs an analog to digital conversion of each selected analog sensor output signal. In this embodiment the output M of circuit 34 is a digital word transmitted in series to plug D3 of interface 26, which is in turn passed to the processor circuit 20 by the intermediary of logic circuit 28. One advantage of this construction is that the analog to digital conversion in alternate circuit 34 can be performed at a higher rate, and at a higher resolution, than is used in ADC 18 of conventional Holter device (or independently of ADC 18 in the case that both the Holter recording and the complementary parameter recording are being performed). Another advantage is that resulting digital word maybe, e.g., 8 bits, and is serially transmitted through or single plug D3 of the interface 26. This provides for an extremely flexible adaptation of the Holter device 10 including the programmable interface 26, which has a small number of programmable plugs, e.g., three—D1, D2 & D3—to record far more complex physiological signals requiring many more leads, e.g., an EEG signal. This is achieved by the use of an alternate circuit 34 that performs the multiplexing and digital conversion of the sensed analog signals. It also should be understood that when the sampling rate of the complementary signal is suitable, the mixed plug may be programmed to transfer analog signals, which are digitized by ADC 18 as described.

The circuit in FIG. 5 illustrates the case of an active external system controlled by the Holter recording machine 10 via the interface connector 26 and logic circuit 28. Plugs X, Y and Z (inputs or outputs) of this system are respectively connected to plugs D1, D2 and D3, so as to manage a data exchange in a desired manner and according to the type of external system concerned. This system can be, for example, and of course without limitation, a drug pump, a communication antenna for an active implantable medical device (cardiac pacemaker, defibrillator, etc.), an implantable prosthesis, a system of teletransmission of Holter recordings to a distant site by a radio/modem, etc.

The programmable interface 26 of the preset invention advantageously allows, by very simple means, to attach to a typical classic Holter machine an extension interface of plugs increasing in a very important manner the utilization and possibility areas of application of a such machine.

The preferred embodiments illustrated and described with respect to the drawings herein are given by way of example only and not by way of limitation. In view of the above description, it will be understood by a person of ordinary skill in the art to make various modifications and changes without departing from the spirit and scope of the present invention.

I claim:

1. An apparatus (10) for recording a physiological signal, comprising:
   a first analog signal input for accepting one or more first signals corresponding to said physiological signal,
   a first set of plugs (14) adapted to receive one or more of said first signals, wherein said first signals are to be recorded;
   a processing circuit for recording data corresponding to said first signals; and
   a programmable interface adapted for transferring one or more second signals comprising:
   at least one voltage supply plug,
   at least one ground plug,
   at least one digital plug, operatively connected to the processing circuit,
   at least one mixed input/output analog/digital (MAD) plug connected to said first analog signal input, and
   a logic circuit operable to control a transfer of said second signals at the programmable interface, wherein the MAD plug is operatively connected to said logic circuit.

2. The apparatus of claim 1, further comprising an analog sensor having an analog signal output connected to the MAD plug, wherein the logic circuit is operable to program the MAD plug as an analog input plug operable to receive said analog sensor analog signal output and transfer said analog sensor analog signal output to the first analog signal input.

3. The apparatus of claim 1, further comprising one of a digital sensor and a digital external circuit connected to the interface, wherein the logic circuit is operable to program the MAD plus as a digital plug operable to transfer therethrough one of a digital input signal corresponding to an output of the digital sensor and a digital output signal corresponding to a digital control signal of an external circuit.

4. The apparatus of claim 1, in which the logic circuit is operable to program said at least one digital plug as one of a signal input plug and a digital output signal.

5. The apparatus of claim 1, wherein the logic circuit is operable to program said at least one digital plug as a sensor recognition plug, said logic circuit having an interrogation signal output to said one digital plug, said logic circuit further being operable to sense a response to said interrogation signal output and determine from said response whether or not an external sensor is connected to said programmable interface.

6. The apparatus of the claim 1 further comprising a multiplexor and a plurality of selection codes corresponding to a plurality of external sensors, wherein the logic circuit is operable to program said at least one digital plug as an output plug, said logic circuit further being operable to emit one of said plurality of said selection codes on said digital plug adaptable to control said multiplexor the multiplexor being operable to select one of said plurality of external sensors.

7. The apparatus of claim 1, wherein the logic circuit is operable to program said at least one digital plug as an output plug, said logic circuit further being operable to emit a sampling control code signal output on said digital plug.

8. The apparatus of claim 1, wherein the logic circuit is operable to program said at least one digital plug as an output plug, said logic circuit further being operable to emit a synchronization clock signal at said digital output.

9. The apparatus of claim 1, wherein the logic circuit further comprises a programmable logic circuit system.

10. In a Holter machine for recording a physiological signal including a first interface having a plurality of plugs, an amplifier having an input coupled to at least one of said plurality of plugs and an output, an analog-to-digital converter having an analog input operatively connected to said amplifier output to sample analog signals and convert sampled analog signals to a digital signal, and a processor operable to operate said analog-to-digital converter and process said digital signals to obtain a signal representative of said physiological signal and record said obtained signal in a memory, wherein the improvement comprises:
   a second interface having a second plurality of plugs, said second plurality of plugs including at least one digital signal plug and at least one mixed plug, said mixed plug having an input/output analog operating mode and an input/output digital operating mode and being operatively connected to said analog-to-digital converter; and
   a logic circuit connected to said mixed plug and said digital plug and to said processor, said logic circuit being operable to control a transmission of signals through said second interface.

11. The apparatus of claim 10 further comprising an external analog sensor having an analog output connected to said mixed plug, wherein the analog output of said external sensor is connected to said analog-to-digital converter.

12. The apparatus of claim 11 wherein said at least one digital plug is connected to said external sensor and said logic circuit is operable to transfer a digital signal through said one digital plug to said external sensor and to sense an analog response of said external sensor at said mixed plug.

13. The apparatus of claim 12 wherein said analog response further comprises a signal identifying the external sensor connected to said second interface.

14. The apparatus of claim 10 further comprising a multiplexor coupled to said logic circuit through said second interface and a plurality of external analog sensors coupled to said multiplexor, each external analog sensor having an analog output connected to said multiplexor, said multiplexor having a common output connected to 'said mixed plug, wherein the logic circuit is operable through said second interface to control the multiplexor to select one of the plurality of analog external sensors and transfer the analog output of said one selected external sensor to said analog-to-digital converter.

15. The apparatus of claim 14 wherein said logic circuit further comprises a digital select signal connected to said at least one digital plug, said multiplexor having a select input connected to said at least one digital plug, wherein said digital select signal operates to select said one selected external analog sensor.

16. The apparatus of claim 15 wherein said digital select signal is a series stream of bits.

17. The apparatus of claim 15 wherein said second interface further comprises at least a second digital plug connected to said multiplexor, wherein said logic circuit is operable to transfer a second digital signal through said second digital plug to said multiplexor and to sense a response of said multiplexor at said mixed plug.

18. The apparatus of claim 10 further comprising an external device connected to said second interface including the at least one digital plug, wherein said logic circuit is operable to transmit at least one digital control signal through said at least one digital plug to operate said external device.

19. The apparatus of claim 18 wherein said at least one digital control signal is one of a synchronization signal and a sampling control signal.

20. The apparatus of claim 19 wherein said at least one digital control signal further comprises a series string of bits, each bit having one of a logical high value and a logical low value.

21. The apparatus of claim 19 wherein the external device further comprises a digital sensor having a unique identification code, and a digital output, wherein said sampling control signal further comprises a series string of bits representing a unique code corresponding to said unique identification code, said external digital sensor being operable to output said digital output to said second interface in response to said series string of bits.

* * * * *

UNITED STATES PATENT AND TRADEMARK OFFICE
CERTIFICATE OF CORRECTION

PATENT NO. : 5,669,393
DATED : September 23, 1997
INVENTOR(S) : Faisandier

It is certified that error appears in the above-identified patent and that said Letters Patent is hereby corrected as shown below:

Column 2, line 32, after "plug $D_i$ ( " insert --$i$--.

Signed and Sealed this

Fifteenth Day of December, 1998

Attest:

BRUCE LEHMAN

*Attesting Officer*     *Commissioner of Patents and Trademarks*